(12) United States Patent  (10) Patent No.: US 7,911,601 B2
Uto et al.  (45) Date of Patent: Mar. 22, 2011

(54) APPARATUS AND METHOD FOR INSPECTING PATTERN

(75) Inventors: Sachio Uto, Yokohama (JP); Minoru Yoshida, Yokohama (JP); Toshihiko Nakata, Hiratsuka (JP); Shunzi Maeda, Yokohama (JP); Atsushi Shimoda, Hiratsuka (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 12/263,682

(22) Filed: Nov. 3, 2008

(65) Prior Publication Data

US 2009/0066943 A1  Mar. 12, 2009

Related U.S. Application Data

(63) Continuation of application No. 11/488,620, filed on Jul. 19, 2006, now Pat. No. 7,446,866, which is a continuation of application No. 10/979,169, filed on Nov. 3, 2004, now Pat. No. 7,081,953, which is a continuation of application No. 10/050,778, filed on Jan. 18, 2002, now Pat. No. 6,831,737.

(30) Foreign Application Priority Data

Jul. 27, 2001 (JP) ................................. 2001-228166

(51) Int. Cl.
 *G01N 21/00* (2006.01)
(52) U.S. Cl. ............... 356/237.5; 356/237.1; 356/237.2
(58) Field of Classification Search ..... 356/237.1–237.5
 See application file for complete search history.

(56) References Cited

U.S. PATENT DOCUMENTS

| | | | | |
|---|---|---|---|---|
| 5,001,873 A | * | 3/1991 | Rufin | 451/39 |
| 5,197,078 A | * | 3/1993 | Terada et al. | 372/55 |
| 5,373,523 A | * | 12/1994 | Fujimoto et al. | 372/59 |
| 5,581,348 A | | 12/1996 | Miura et al. | |
| 5,767,962 A | | 6/1998 | Suzuki | |
| 5,796,484 A | | 8/1998 | Honma | |
| 5,963,314 A | | 10/1999 | Worster | |
| 6,151,350 A | * | 11/2000 | Komori et al. | 372/59 |
| 6,219,367 B1 | * | 4/2001 | Atsumi | 372/59 |
| 6,532,100 B1 | * | 3/2003 | Partanen et al. | 359/326 |
| 6,556,286 B1 | | 4/2003 | LaFontaine et al. | |
| 6,556,290 B2 | * | 4/2003 | Maeda et al. | 356/237.2 |

(Continued)

FOREIGN PATENT DOCUMENTS

JP  62-286226  12/1987

(Continued)

OTHER PUBLICATIONS

U.S. Appl. No. 09/764,457, filed Jan. 2001, Uto.

*Primary Examiner* — Michael P Stafira
(74) *Attorney, Agent, or Firm* — Antonelli, Terry, Stout & Kraus, LLP.

(57) ABSTRACT

A method and apparatus for inspecting defects includes emitting an ultraviolet light from an ultraviolet light source, illuminating a specimen with the ultraviolet light in which a polarization condition of the ultraviolet light is controlled, controlling a polarization condition of light reflected from the specimen which is illuminated by the polarization condition controlled ultraviolet light, detecting the light reflected from the specimen, processing the detected light so as to detect defects, and outputting information about the defects. The ultraviolet light source is disposed in a clean environment supplied with clean gas and separated from outside.

8 Claims, 8 Drawing Sheets

U.S. PATENT DOCUMENTS

| | | |
|---|---|---|
| 6,587,194 B2 | 7/2003 | Karpol et al. |
| 6,633,376 B1 | 10/2003 | Nishida et al. |
| 6,671,303 B1 * | 12/2003 | Pang ................ 372/59 |
| 6,721,345 B2 * | 4/2004 | Bragin et al. ............ 372/58 |
| 6,738,406 B2 * | 5/2004 | Vogler ................ 372/60 |
| 6,757,316 B2 * | 6/2004 | Newman et al. ............ 372/57 |
| 6,839,372 B2 * | 1/2005 | Pan et al. ............ 372/55 |
| 6,963,595 B2 * | 11/2005 | Rule et al. ............ 372/55 |
| 7,081,953 B2 | 7/2006 | Uto et al. |
| 2001/0012311 A1 * | 8/2001 | Atsumi ............ 372/59 |

FOREIGN PATENT DOCUMENTS

| | | |
|---|---|---|
| JP | 03-167885 | 7/1991 |
| JP | 04-025147 | 1/1992 |
| JP | 5-157542 * | 6/1993 |
| JP | 05-335393 | 12/1993 |
| JP | 7-015061 | 1/1995 |
| JP | 8-006082 | 1/1996 |
| JP | 09-162117 | 6/1997 |
| JP | 11-064902 | 3/1999 |
| JP | 11-087814 | 3/1999 |
| JP | 11-167132 | 6/1999 |
| JP | 2000-133585 | 5/2000 |
| JP | 2001-165861 | 6/2001 |
| JP | 2001-176942 | 6/2001 |
| JP | 2001-194323 | 7/2001 |

* cited by examiner

APPARATUS AND METHOD FOR INSPECTING PATTERN

CROSS REFERENCE TO RELATED APPLICATION

This is a continuation of U.S. application Ser. No. 11/488,620, filed Jul. 19, 2006, now U.S. Pat. No. 7,44,866 which is a continuation of U.S. application Ser. No. 10/979,169, filed Nov. 3, 2004, now U.S. Pat. No. 7,081,953, which is a continuation of U.S. application Ser. No. 10/050,778, filed Jan. 18, 2002, now U.S. Pat. No. 6,831,737, the subject matter of which is incorporated by reference herein.

BACKGROUND OF THE INVENTION

The present invention relates to a high resolution optical system suitable for use in inspections and observations of micro pattern defects and foreign materials or the like typified in a semiconductor device manufacturing process and a flat panel display manufacturing process, and a pattern defect inspecting apparatus using the same.

With high integration of a semiconductor, circuit patterns show an increasing tendency to scale down. Under such a tendency, there has been an increasingly demand for a high resolution-based detection of pattern defects on a wafer to which masks and reticles used upon manufacturing a semiconductor device in a photolithography process, and circuit patterns formed on these, are transferred by exposure. As means for enhancing the resolution, may be mentioned a way to bring the wavelength of illumination light from visible light to ultraviolet light.

A mercury lamp has heretofore been used as a light source. Only required wavelengths were used by being optically selected from various emission lines held by the mercury lamp.

However, a problem arises in that each emission line of the mercury lamp is broad in light-emitting spectrum width and the correction of chromatic aberration of an optical system falls into difficulties, and a light source is scaled up to obtain a sufficient illumination intensity, thereby causing a decrease in efficiency and the like.

An exposure device equipped with a 248 nm-wavelength KrF excimer laser has recently been developed as a light source used for the exposure device upon semiconductor manufacture. However, the light source for the excimer laser is large in size and expensive. Further, a problem arises from the viewpoint of maintenance such as the need for predetermined safety measures because noxious fluorine gas is used.

As ultraviolet laser light sources, may be mentioned, for example, a laser device for wavelength-converting a solid YAG laser light beam by a non-linear optical crystal, an Ar-Kr laser device, etc. Each of them can obtain ultraviolet laser light having a wavelength which ranges from 266 nm to 355 nm.

However, while these ultraviolet laser light sources respectively have the advantage of obtaining a high output as compared with a lamp used as a light source, they have coherence. When the ultraviolet laser light is illuminated to a circuit pattern, unnecessary coherent patterns (speckle noise) occur and hence they exert a bad influence on the inspection of the circuit pattern.

Increasing the resolution of a circuit pattern to be detected needs to set the magnitude of illumination light launched into an objective lens to a suitable magnitude and illuminate a specimen from various angular directions. Since, however, the laser is used as a point source of light, it encounters a difficulty in increasing an illumination angle.

Further, each of the ultraviolet laser light sources wavelength-converts the solid YAG laser light beam by means of the non-linear optical crystal to thereby obtain a third harmonic wave (355 nm) or a fourth harmonic wave (266 nm) of the YAG laser beam. A wavelength converting device for obtaining the UV laser light in this way has been known in each of Japanese Patent Application Laid-Open Nos. Hei 8-6082, Hei 7-15061, Hei 11-64902 and Hei 11-87814. However, when the crystal is irradiated with the laser for long hours, the interior of the crystal is deteriorated and hence the transmittance of the laser beam is significantly reduced. Therefore it is necessary to change a position to irradiate the crystal with the laser after the irradiation thereof for a predetermined time. As viewed from the standpoint of another aspect, Japanese Patent Application Laid-Open No. Hei 8-6082, for example, performs such feedback control that a mirror corresponding to some of a resonator is mounted to a piezoelectric device or the like and displaced to make frequency tuning inside the wavelength converting device, whereby a resonator length is varied to change a resonant frequency. The present publication describes that the fluctuation of the frequency takes place when such frequency tuning is detuned, so that the intensity of output light varies. The variation in the output light is not on the order of an ability to visually confirm it, and is a very momentary variation. However, this becomes a serious problem for an apparatus for inspecting a pattern defect at high speed.

SUMMARY OF THE INVENTION

In order to solve the foregoing problems, an object of the present invention is to provide a pattern defect inspecting apparatus capable of implementing micro patterns with high resolution and realizing a stable pattern defect inspection with a high degree of reliability with ultraviolet laser light as a light source.

In order to achieve the above object, the present invention provides a pattern defect inspecting apparatus, comprising a stage capable of placing a substrate to be inspected thereon and moving in X and Y directions; an ultraviolet laser light source for emitting ultraviolet laser light therefrom; an illumination optical system including a multispot shaper for forming a plurality of light-emitting images from the ultraviolet laser light emitted from the ultraviolet laser light source, a coherence reduction optical system for reducing coherence with respect to the ultraviolet laser light comprised of the plurality of light-emitting images formed by the multispot shaper, and a converging optical system for allowing a plurality of pieces of the ultraviolet laser light reduced in coherence through the coherence reduction optical system to converge on a pupil position of an objective lens, the illumination optical system applying the plurality of pieces of ultraviolet laser light focused on the pupil of the objective lens by the converging optical system onto the substrate to be inspected; a detection optical system including an image forming optical system for focusing an ultraviolet reflected light image from a circuit pattern formed on the substrate to be inspected, and an image sensor for receiving the ultraviolet reflected light image focused by the image forming optical system and converting the same into an image signal; an image signal processing circuit including an A/D converter for A/D converting the image signal obtained from the image sensor of the detection optical system, and a comparator for comparing a detected digital image signal converted by the A/D converter with a reference digital image signal to thereby detect a defect or a defect candidate in the circuit pattern and outputting inspection information in relation to the detected defect or the detected defect candidate; and an amount-of-light monitor unit for allowing some of the ultraviolet laser light emitted from the ultraviolet laser light source to branch off and detecting the intensity thereof.

The present invention also provides the pattern defect inspecting apparatus characterized in that laser speckles are suppressed by the coherence reduction optical system having such a configuration as to form a multi light-emitting image with the multispot shaper provided in an illumination optical path and two-dimensionally scan it on the pupil of the objective lens.

Further the present invention is characterized in that the ultraviolet laser light source comprises a laser device for emitting laser fundamental wave light therefrom, and a wavelength converting device for wavelength-converting the laser fundamental wave light emitted from the laser device into a double wave, both of which are placed in a clean container.

Furthermore the present invention is characterized in that the wavelength converting device comprises a resonator comprised of an optical member having high reflectance, and a non-linear optical crystal placed in a suitable position lying in an optical path of the resonator.

Still further the present invention is characterized in that the amount-of-light monitor unit comprises a division type optical device for measuring the amount of a displacement of an outgoing optical axis of the ultraviolet laser light source.

Still further the present invention is characterized in that the amount-of-light monitor unit monitors a variation in the amount of the ultraviolet laser light during inspection.

Still further the present invention also includes a central processing unit for detecting a malfunction on the basis of the intensity of the ultraviolet laser light detected by the amount-of-light monitor unit and storing the inspection information outputted from the comparator of the image signal processing circuit at a time at which the malfunction is detected, thereby enabling re-inspection.

Still further the present invention further includes a central processing unit for predicting the life of the ultraviolet laser light source and detecting a malfunction thereof, based on the variation in the amount of the ultraviolet laser light detected by the amount-of-light monitor unit to thereby determine whether the inspection should be carried out continuously.

Still further the present invention constitutes a system wherein when the output intensity of the ultraviolet laser light is always detected by the amount-of-light monitor unit and a change in the intensity thereof is greatly varied as compared with a constant reference value, positional coordinates of the stage at that time are stored and fed back to the result of inspection, and when an output value reaches a reference value or less even with respect to an output reduction in ultraviolet laser light with time, a crystal is moved to change a point to apply laser thereto.

Still further the present invention is characterized in that the coherence reduction optical system of the illumination optical system comprises a swinging first optical device or a rotating second optical device placed therein.

Still further the present invention is characterized in that the coherence reduction optical system of the illumination optical system includes a swinging first optical device and a rotating second optical device respectively placed in positions unconjugated with respect to each other.

Still further the present invention is characterized in that the ultraviolet laser light source is covered with a container and a clean gas is circulated through the interior thereof.

Still further the present invention is characterized in that the illumination optical system and the detection optical system are covered with a container and a clean gas is circulated through the interiors thereof.

Still further the present invention is characterized in that the illumination optical system, the detection optical system and the stage are placed on an antivibration table and the ultraviolet laser light source is capable of being placed on the antivibration table by being positioned thereon.

Still further the present invention is characterized in that the coherence reduction optical system of the illumination optical system is configured in a unit and the unit is positioned relative to the illumination optical system to enable the installation thereof.

BRIEF DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

DETAILED DESCRIPTION OF THE PREFERRED EMBODIMENTS

Preferred embodiments of pattern defect inspecting apparatuses and methods thereof according to the present invention will be hereinafter described with reference to FIGS. 1 through 12.

Figure 1:
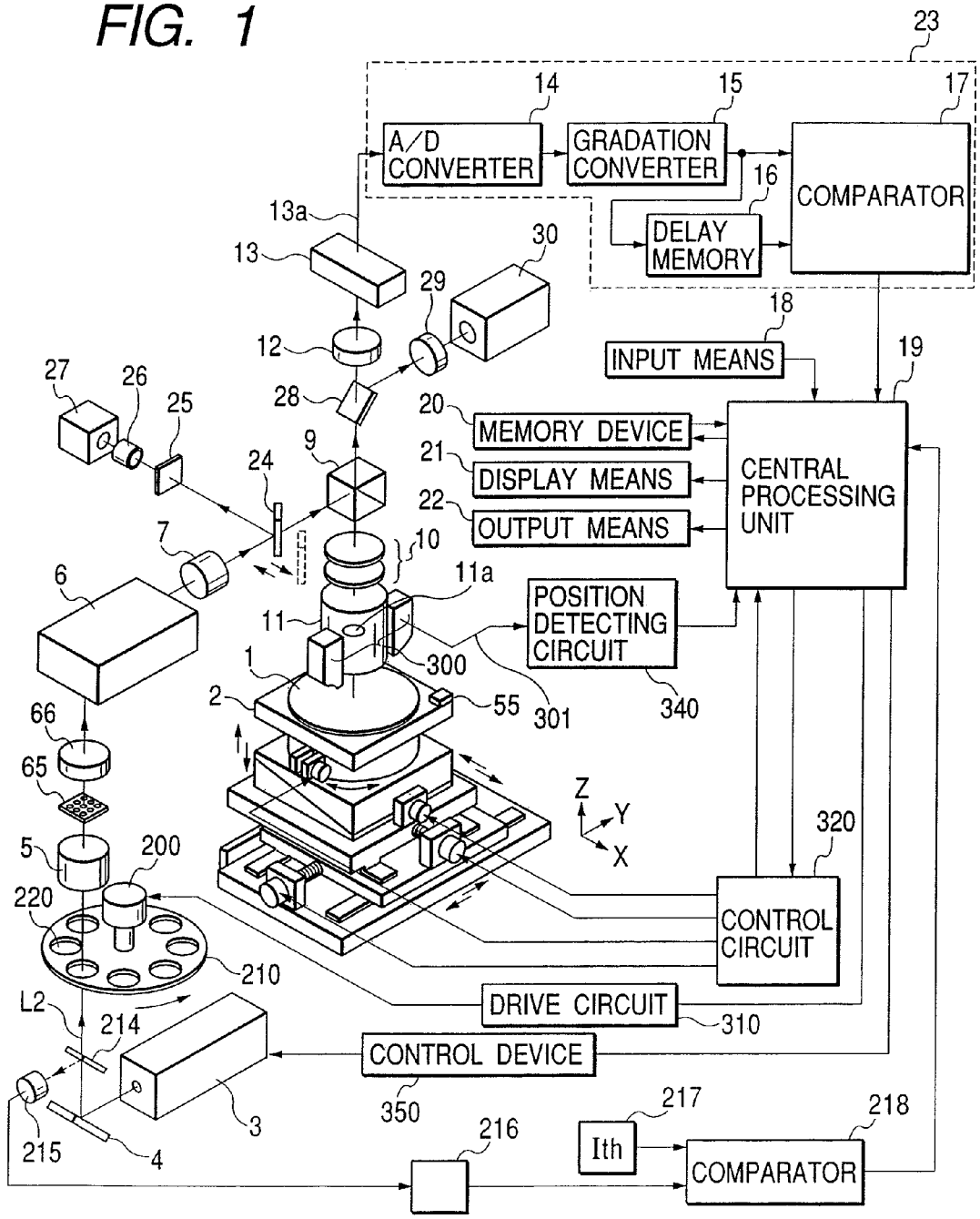
FIG. 1 is a configurational diagram showing a first embodiment of a pattern defect inspecting apparatus according to the present invention.

FIG. 1 is a diagram showing a first embodiment of a pattern defect inspecting apparatus according to the present invention. In the present invention, an ultraviolet laser light source (ultraviolet laser generating device) 3 for emitting DUV laser light is provided to carry out high-luminance illumination in a DUV region. A stage 2 has degrees of freedom in X, Y, Z and θ directions and places an inspected object (e.g., a semiconductor wafer) formed with an inspected pattern thereon as a specimen 1. Further, the stage 2 is connected to a central processing unit 19 through a stage control circuit 320.

An illumination optical system for illuminating a DUV laser light beam on the specimen 1 comprises an ultraviolet laser light source 3 which increases a source voltage for excitation laser light L1 under the control of a control device 350 to thereby perform an output adjustment to the excitation laser light L1 and which comprises a laser device 80 and a wavelength converting device 81, a detector (amount-of-light or light intensity monitor means) 215 which is placed in an optical path of the laser light emitted from the ultraviolet laser light source 3 and allows the intensity of some laser light free of trouble upon inspection using the laser beam to branch by a mirror 214, followed by detection thereof, a density adjusting device (light intensity adjuster) 210 placed in the illumination optical path, for adjusting the amount of laser light L2, a beam expander 5 for enlarging a laser beam spot, a multispot shaper 65 and a coherence reduction optical system 6 for reducing coherence, a polarizing beam splitter 9 for reflecting polarized laser light, a polarizing devices group 10, and an objective lens 11.

The illumination optical system is further provided with an observation optical system 25 through 27 capable of observing the DUV laser light.

A detection optical system for detecting an ultraviolet reflected-light image from the specimen 1 comprises the objective lens 11, the polarizing devices group 10, the polarizing beam splitter 9 for allowing the reflected light to pass therethrough, an image forming lens 12, and an image sensor 13. The detection optical system is further provided with an observation optical system 29 and 30 capable of observing a spatial image for a pupil 11a of the objective lens 11.

Owing to the above construction, the ultraviolet laser light L2 emitted from the ultraviolet laser light source 3 is launched into the objective lens 11 through a mirror 4, the mirror 214, the density adjusting device (light intensity adjuster) 210 equipped with a large number of density filters 220 having transmittances different from one another, the beam expander 5, the multispot shaper 65, a lens 66, the coherence reduction optical system 6, a lens 7, the polarizing beam splitter 9 and the polarizing devices group 10 and is applied onto an inspected object 1 formed with an inspected pattern. The laser light L2 whose light flux is expanded with the beam expander 5, is focused on the neighborhood of the pupil 11a of the objective lens 11 by means of the lens 7, followed by application onto the specimen 1.

The ultraviolet reflected light from the specimen 1 is detected by the image sensor 13 through the objective lens 11, the polarizing devices group 10, the polarizing beam splitter 9 and the image forming lens 12 as viewed vertically from above the specimen 1. The polarizing beam splitter 9 has the function of reflecting the light when the polarizing direction of the laser light is parallel to its reflected surface (as viewed in an X direction) and allowing it to pass therethrough when it is vertical thereto. In the present embodiment, the polarizing beam splitter 9 is placed in such a manner that the laser light L2 is totally reflected.

The polarizing devices group 10 has the function of changing polarizing conditions for the ultraviolet laser illumination light and the ultraviolet reflected light from the specimen 1. Meanwhile, in the case of the DUV laser light, the intensity of the reflected light thereof subtly changes according to the shape of an inspected pattern formed on the specimen 1 and the difference in density thereof. Therefore the polarizing devices group 10 adjusts a polarization ratio of the illumination light so that the difference in the intensity of light reflected from the pattern does not reach the image sensor 13 as the unevenness of lightness, and comprises a ½-wavelength plate 10a and a ¼-wavelength plate 10b for applying a change in phase to the illumination light. When the ¼-wavelength plate 10b is turned 450 about the optical axis, for example, the illumination light is brought to circularly polarized light and applied to the specimen 1. Further, since the reflected light passes through the ¼-wavelength plate 10b twice, it is placed in the direction of polarization orthogonal to the illumination light and passes through the polarizing beam splitter 9, followed by arrival onto the image sensor 13.

The image sensor 13 comprises, for example, a storage type image sensor (e.g., a TDI sensor or the like) having detection sensitivity for the DUV region and outputs a density image signal 13a corresponding to the lightness (light and shade or density) of the light reflected from the inspected pattern formed on the specimen 1. Namely, the image sensor 13 detects lightness information (density signal 13a) of the inspected pattern formed on the specimen 1 while the stage 2 is moving in a Y direction to move the specimen 1 at a constant speed.

A focal-point detection optical system 300 is used to detect a displacement of the specimen 1 as viewed in a Z direction while the stage 2 is being moved. A signal 301 detected by the focal-point detection optical system 300 is inputted to a central processing unit 19 through a position detecting circuit 340. The central processing unit 19 drives the stage 2 through a stage control circuit 320 in such a manner that the surface of the specimen 1 is always placed in a focusing focal position, and sets its position by offsetting as a focal position detected by using a reference specimen 55 placed in a position free of interfere upon inspection, thereby making it possible to carry out focal-point focusing control at an arbitrary position of a thin-film surface formed on the specimen 1. Thus the density image signal 13a obtained from the image sensor 13 is inputted to an image signal processing circuit 23 where a detect inspection for a circuit pattern is performed.

The image signal processing circuit 23 comprises a A/D converter 14, a gradation converter 15, a delay memory 16 for forming a reference image signal and a comparator 17, etc.

The A/D converter 14 converts the density image signal 13a obtained from the image sensor 13 into a digital image signal. The gradation converter 15 comprises, for example, a 8-bit gradation converter and effects such gradation or tone conversion as described in Japanese Patent Application Laid-Open Hei 8 (1996)-320294 on the digital image signal outputted from the AND converter 14. Namely, the gradation converter 15 performs logarithmic, exponential and polynomial conversions, etc. to thereby correct a thin film formed on the inspected object 1, such as a semiconductor wafer or the like in a process, and the unevenness of lightness of an image produced by interference of a laser light beam.

The delay memory 16 stores and delays an image signal outputted from the gradation converter 15 with a scanning width of the image sensor 13 by one cell, one chip (one die) or one shot repeatedly configured on the specimen 1 to thereby form a reference image signal used as the reference for comparison.

The comparator 17 compares the detected image signal outputted from the gradation converter 15 with the reference image signal obtained from the delay memory 16 and detects a portion determined as inconsistency on the basis of a criteria for determination as a defect or a defect candidate. Namely, the comparator 17 is used to compare a reference image signal delayed by an amount equivalent to a cell pitch or a die pitch or the like outputted from the delay memory 16, with a detected image signal. In short, the comparator 17 detects a defect candidate such as a pseudo defect or the like without detecting a true defect in relation to the detection of a defect of from about 20 nm to about 50 nm by the DUV laser light. It is further necessary to analyze the defect candidate in detail by use of a review apparatus (e.g., a SEM length measuring apparatus, a SEM visual inspecting apparatus or the like). Incidentally, the details of the comparator 17 may be one disclosed in Japanese Patent Application Laid-Open No. Sho 61 (1986)-212708, for example. The comparator 17 comprises, for example, an image registration circuit, a difference image detecting circuit for detecting a difference between the aligned or registered images, an inconsistence detecting circuit for binarizing or digitizing the difference image, a feature extracting circuit for extracting an area, a length, coordinates, etc. from the digitized output, etc.

The central processing unit 19 is used to control and process the whole pattern defect inspecting apparatus. Further, the central processing unit 19 takes input thereto of coordinates such as sequence data obtained based on design information, on the specimen 1 such as the semiconductor wafer by input means 18 comprising a keyboard, a recording medium, a network or the like, thereby creating defect inspection data on the basis of the result of comparison and inspection by the comparator 17 according to the input coordinates such as the sequence data or the like on the specimen 1 and allowing a memory device 20 to store the data therein. The defect inspection data can also be displayed on display means 21 such as a display as needed. Further, the data is outputted to output means (including a network as well) 22, where a defective point can also be observed through the use of another review apparatus or the like, for example.

An embodiment of the ultraviolet laser light source (ultraviolet laser light generating device) 3 will next be explained. Obtaining high resolution needs to bring the wavelength into short-wavelength form. An improvement in inspection speed needs to high-luminance illumination. For example, a discharge lamp such as mercury xenon or the like is used as illumination means. Of an emission spectrum (emission line) of the lamp, a visible region is extensively used to obtain a light intensity. However, a light intensity based on an emission line in each of ultraviolet and deep ultraviolet regions is only a few percentages as compared with a broad band for visible light. A large light source is needed to ensure a desired light intensity. There are restrictions such as the provision of a lamp light source away from an optical system for the purpose of taking all possible measures against radiation when the lamp light source is used, and preventing the transfer of heat to the optical system since the lamp light source generates heat. In the present invention, ultraviolet laser light (DUV: Deep Ultraviolet Rays) capable of easily ensuring a short wavelength is set as the light source 3 from such a viewpoint. The ultraviolet laser light indicates laser light whose wavelength ranges from about 100 nm to about 400 nm, whereas the DUV laser light indicates laser light whose wavelength ranges from about 100 nm to about 314 nm.

Figure 2:
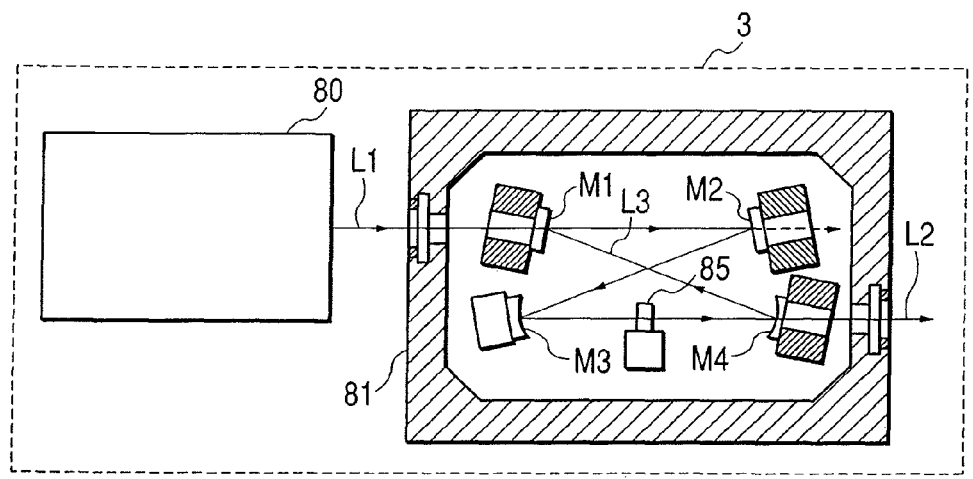
FIG. 2 is a diagram illustrating a schematic configuration of an ultraviolet laser light source according to the present invention.

The ultraviolet laser light source (ultraviolet laser generating device) 3 comprises a laser device 80 for emitting a laser fundamental wave light L1 having a wavelength of 532 nm, for example, and a wavelength converting device 81 for changing the fundamental wave light L1 into a double wave as shown in FIG. 2 by way of example. The wavelength converting device 81 includes mirrors M1 through M4 placed thereinside. Excitation laser light L1 emitted from the laser device 80 passes through the mirror M1 so as to reach the mirror M2. The mirror M2 allows some of the incident light to pass therethrough and reflects the remainder therefrom. The laser light reflected by the mirror M2 reaches the mirror M3. A non-linear optical crystal 85 is placed in an optical path between the mirrors M3 and M4. The laser light totally reflected by the mirror M3 passes through the non-linear optical crystal 85 so as to reach the mirror M4. An optical member comprising these mirrors M1 through M4 and having high reflectance constitutes a resonator. Further, since the non-linear optical crystal 85 is placed in an optically-calculated suitable position, the incident light L1 of 532 nm is converted into a second harmonic wave L2 having a wavelength of 266 nm by the crystal 85. Only the ultraviolet laser light L2 of the second harmonic wave is outputted through the mirror M4. Namely, reflecting coating is applied to the mirror M4 so that the second harmonic wave is transmitted therethrough and waves other than that are reflected. Laser light L3 non-converted by the non-linear optical crystal 85 is reflected by the mirror M4 so as to reach the mirror M1. The laser light L3 then traces the same optical path again as the laser light L1 having passed through the mirror M1. Here, some incident light transmitted through the mirror M2 is one for synchronizing the frequency of the incident light with the resonance frequency of the wavelength converting device 81 in such a manner that an error therebetween is detected by unillustrated detecting means and both are always kept in a resonant state. By means of an unillustrated servo mechanism (e.g., an actuator such as a piezoelectric device), the mirror M3, for example, is precisely moved at high speed to control a resonator length with high accuracy and thereby electrically feed it back so as to produce stable resonance. Simultaneously, the laser light L1 launched into the wavelength converting device 81 is also controlled by an unillustrated mirror serve mechanism provided in the laser device 80 so that the laser light L1 always coincides with the optical axis of the wavelength converting device 81.

The ultraviolet laser light L2 of 266 nm outputted from the wavelength converting device 81 has ability coherence and leads to the occurrence of speckles (interference patterns) when laser is illuminated to the circuit pattern on the inspected object 1. Thus it is necessary to reduce the coherence upon illumination of the ultraviolet laser light L2. In order to reduce the coherence, either of time coherence and spatial coherence may be reduced.

Figure 3:
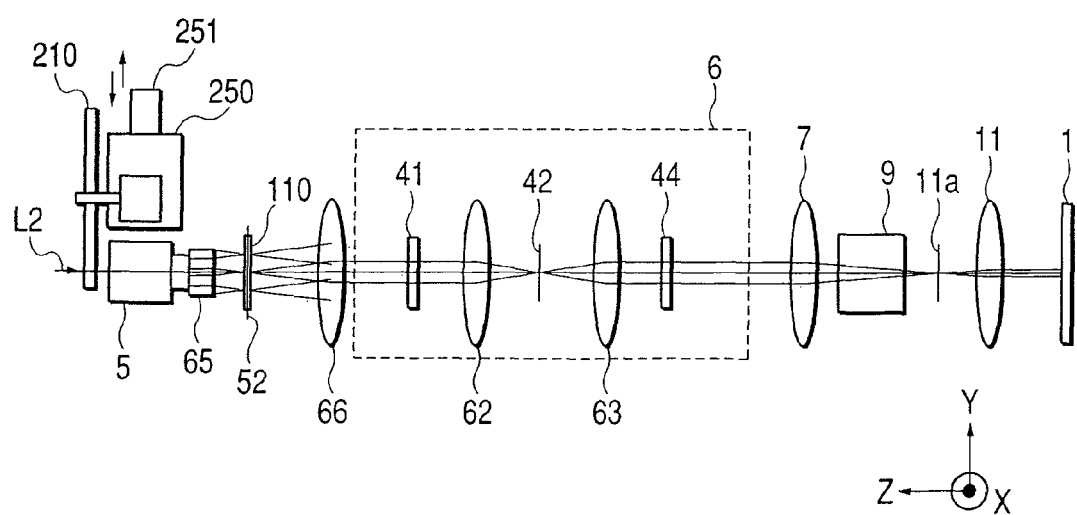
FIG. 3 is a typical diagram depicting an illumination optical system according to the present invention.

Thus the coherence reduction optical system 6 is used to reduce the spatial coherence in the present invention. FIG. 3 is a typical diagram showing one embodiment of an illumination optical system including the coherence reduction optical system 6 according to the present invention, and FIG. 4 is a perspective view showing one embodiment of the coherence reduction optical system 6, respectively.

In the present invention, two scan mirrors 41 and 44 (swinging optical devices) orthogonal to each other, which are provided in an optical path, two-dimensionally scan ultraviolet laser light to thereby reduce coherence. Namely, ultraviolet laser light L2 emitted from an ultraviolet laser light source 3 is expanded to a given magnitude by a beam expander 5, which in turn is launched into a multispot shaper 65, where a plurality of laser spots (multispot image) are formed at a focal position 52 of the multispot shaper 65. Afterwards, the ultraviolet laser light L2 is focused on a pupil 11a of an objective lens 11 through lenses 66, 62 and 63, a lens 7 and a polarizing beam splitter 9. Meanwhile the focal position 52 of the multispot shaper 65 is conjugated with respect to a focal position 42 for the lenses 62 and 63 and the pupil 11a of the objective lens 11. Further, the reflected surfaces of the mirrors 41 and 44 are conjugated with respect to the surface of a specimen 1.

Figure 4:
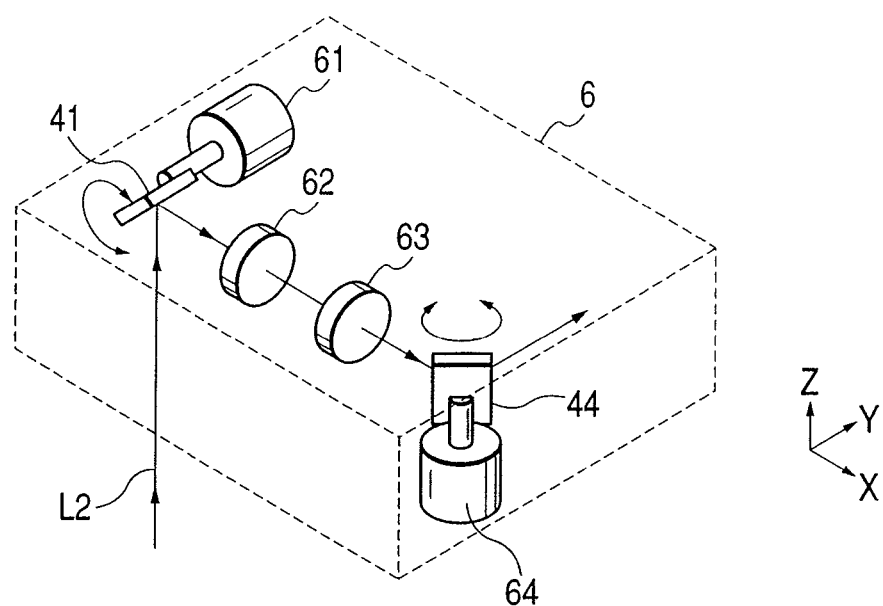
FIG. 4 is a diagram for describing one embodiment of an optical system for reducing spatial coherence of an ultraviolet laser beam illumination according to the present invention.
Figure 5A:
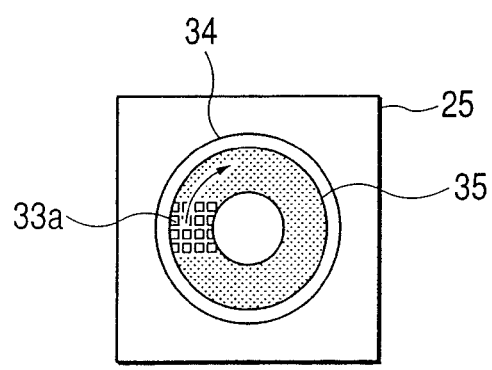
FIGS. 5($a$) and 5($b$) are diagrams for describing the condition of illumination on an objective lens pupil by the ultraviolet laser beam illumination according to the present invention.

Multispot light (shown in FIG. 5(a)) formed at the focal position 52 of the multispot shaper 65 is two-dimensionally scanned on the pupil 11a of the objective lens 11 by means of the mirrors (swinging optical devices) 41 and 44 mounted to reciprocatingly rotated motors 61 and 64 shown in FIG. 4. The motors 61 and 64 are reciprocatingly rotated according to the continuous input of an electric signal such as a triangular wave, a sine wave or the like. A turning angle of each motor is changed according to a change in the width of a signal waveform, whereby a scan trajectory on the pupil 11a of the objective lens can be adjusted to change illumination conditions (illumination sigma).

Figure 5B:
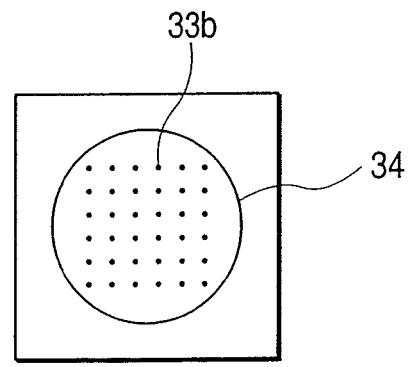

However, the ultraviolet laser light used as the light source is invisible light and invisible. Thus as shown in FIG. 1, the mirror 24 is placed in the illumination optical path to cause the optical path to branch off. Thereafter, the scan trajectory of the laser light is projected onto the screen 25 to enable its observation. The screen 25 is placed in a position conjugated with respect to the pupil 11a of the objective lens. The screen 25 has the action of emitting fluorescence according to the radiation of the ultraviolet light and is capable of obtaining such a laser scan trajectory 35 as shown in FIG. 5(a). The laser scan trajectory 35 on the screen 25 is detected by the lens 26 and TV camera1 27. In such a case as shown in FIG. 5(b), a diffusion plate (rotating optical device) 50 is rotated at high speed as will be described later to thereby make it possible to reduce coherence of multispot light 33b. Incidentally, designated at numerals 34 in FIGS. 5(a) and 5(b) respectively indicate pupils 11a of objective lenses 11.

The magnitudes or sizes of the multispot light 33a and 33b formed in the pupils 11a of the objective lenses 11 are determined according to the ratio between the focal distances of the lens 66 and lens 7. Therefore some of the illumination optical system including the coherence reduction optical system 6 is changed into unitization or replaced with another to thereby make it possible to change the magnitudes of the multispot light 33a and 33b formed in the pupils 11a (34) of the objective lenses 11. In this case, the optical length extending from the focal position 52 of the multispot shaper 65 to its corresponding pupil 11a of the objective lens is set so as to remain unchanged.

FIG. 5(a) is a reduced or scaled-down example of the multispot light 33, and FIG. 5(b) is an enlarged example of the multispot light 33, respectively. When the multispot light 33 is scaled down, the illumination sigma can be varied with a change in the amplitude of the waveform of a drive signal inputted to each of the motors 61 and 64. On the other hand, when the illumination sigma is scaled up, the amplitude of the waveform of the drive signal inputted to each of the motors 61 and 64 can be reduced. Further, for example, a circular aperture stop is provided at a position (e.g., the focal position 42 of the lens 62) conjugated with respect to the pupil 11a of the objective lens 11 to restrict light flux of laser, whereby the illumination sigma can be changed.

On the other hand, it is necessary to thinly narrow down the diameter of each multispot light 33 on the pupil 11a of each objective lens 11 for the purpose of increasing an illumination visual field on the specimen 1 as large as possible. Further, an increase in the number of multispots and high-speed rotation are needed to bury the pupil 11a of the objective lens 11 by the multispot light 33 from thereabove.

Figure 6A:
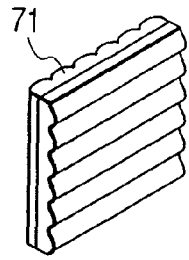
FIGS. 6($a$) to 6($c$) are diagrams for describing an embodiment of an optical device for forming a multi light-emitting image (spot image) according to the present invention.
Figure 6B:
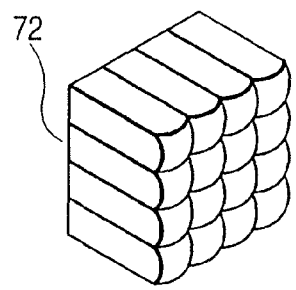
Figure 6C:
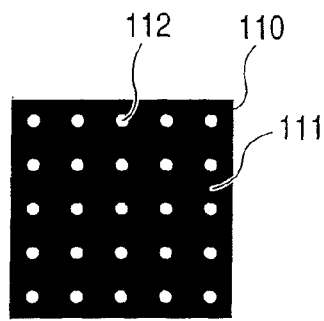

In the laser scan example shown in FIG. 5(a), scanning may preferably be carried out at least once or a whole number of times within a storage time of the image sensor 13. A drive signal may be supplied from outside through a signal generator. As one example, a scan trajectory may be set so as to reach at least one scan or more within the storage time of the image sensor 13 through the use of a clock pulse or the like of a linear encoder for coordinate position control, which is provided at the stage 2. Incidentally, as multispot forming means, for example, even one can be achieved wherein a cylindrical lens array 71 shown in FIG. 6(a) is placed in a vertical form, or a rod lens 72 is placed on a two-dimensional basis (see FIG. 6(b)). In this case, a mask 110 (see FIG. 6(c)) comprised of transmissive portions 112 and a light-shielding portion 11 is placed in the focal position 52 of the multispot shaper 65 to enable the removal of stray light other than spots. Changing the curvature of a lens in an orthogonal direction enables even rectangular illumination.

Here, the ultraviolet laser light used as the light source has linear polarization. Since the resolution of the optical system changes according to the illumination or the polarized state of detection, the polarizing devices 10a (e.g., ½-wavelength plate) and 10b (e.g., ¼-wavelength plate) placed in the optical path are respectively rotatably constructed and detect polarized light in a specific direction, of reflected light emitted from a circuit pattern formed on the specimen 1 in accordance with a semiconductor process.

Incidentally, the mirror 28, lens 29 and detector 30, which are provided in the optical path extending from the polarizing beam splitter 9 to the image sensor 13, are used to detect spatial images on a pupil surface of the objective lens 11.

Figure 7:
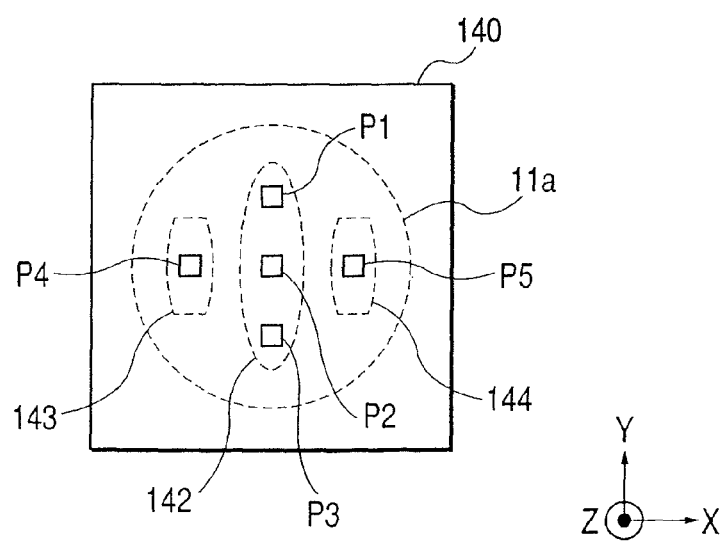
FIG. 7 is a typical diagram showing the state of light reflected from patterns on the objective lens pupil.

FIG. 7 is a typical diagram showing a state in which spatial images 142 through 144 in the pupil 11a of the objective lens 11 are detected as light or bright images by the detector 30 such as the TV camera or the like. Reference numeral 140 indicates a field of view for detection of the detector 30. Reference numeral 142 indicates a bright image of zero-order reflected light (0-order diffraction reflected light: regular reflected light) from a circuit pattern. Reference numerals 143 and 144 respectively indicate bright images of 1-order reflected light (1-order diffraction reflected light). Of these, one largest in the reflected amount of light corresponds to the 0-order reflected light from the surface of the specimen 1. This occurs in excess at a portion where micro patterns on the specimen 1 are in close formation. Since the 1-order reflected light is low in regular reflection component when compared with the 0-order reflected light, its light intensity is low. Thus the uniform or even detection of both by the image sensor 13 needs to make adjustments to the balance between the reflected pieces of light. Attention is now paid to specific regions P1 through P5 of the spatial images detected by the detector 30. The average brightness of each region is calculated by an image processing apparatus (not drawn), and the polarizing device 10 is rotated by drive means (not drawn) so that the 0-order and 1-order reflected pieces of light are made uniform. While this work is made possible by, for example, measuring light reflected from each circuit pattern preformed on the specimen 1 through the use of design data or the like to thereby control the polarizing device 10, the details thereof are determined according to experiments.

Meanwhile in the pattern defect inspecting apparatus according to the present invention, the image sensor 13 detects the brightness information about the inspected pattern formed on the specimen 1 with high accuracy in the state of the specimen 1 being focused on the inspected pattern while the specimen 1 is being moved at the constant speed by the stage 2. The comparator 17 compares the image signal detected with a high degree of accuracy with the reference image signal lying within the delay memory 16, which has been stored by one cell, one chip (die) or one shot, whereby the inconsistent portion is detected as the defect. Therefore when, for example, the lightness unevenness of an image due to a variation in the amount of illumination light occurs in either of the delay image (reference image signal) outputted from the delay memory 16 and the detected image signal, the normal portion of the circuit pattern is determined as a defect, thereby causing a possibility of misdetection. As factors responsible for the lightness unevenness, there are considered a variation in the amount of ultraviolet laser light emitted from the ultraviolet laser light source 3, etc.

The ultraviolet laser light source 3 is one wherein as described above, the laser fundamental wave light L1 is launched into the non-linear optical part 85 provided inside the wavelength converting device 81 and caused to pass therethrough, thereby obtaining the second harmonic wave having the wavelength corresponding to one half that of the incident light. In order to obtain stable oscillations of the ultraviolet laser light, the error between the frequency of the incident light from the laser device 80 and the resonant frequency of the wavelength converting device 81 is detected, and the servo mechanism using the actuator such as the piezoelectric device or the like is electrically fed back so that the two are always kept in the resonant state, thereby allowing the optical axis thereof to coincide with the laser light. Thus the ultraviolet laser light source is so delicate thereinside.

Therefore in the pattern defect inspecting apparatus according to the present invention, the central processing unit 19 detects the output of the ultraviolet laser light emitted from the ultraviolet laser light source 3 by means of the detector (amount-of-light or light intensity monitor means) 215 and an integration circuit 216 to thereby detect the malfunction of the ultraviolet laser light source 3 based on a signal obtained from a comparator 218, and feeds back it for inspection. Namely, as shown in FIG. 1, some of the ultraviolet laser light L2 emitted from the ultraviolet light source 3 is reflected by the mirror 214 and then received by the detector 215 comprised of a division type light-detecting device or the like, after which it is compared with a reference value (Ith) 217 by the comparator 218, whereby the malfunction of the ultraviolet laser light source is detected.

FIG. 8 is a typical diagram showing a state in which ultraviolet laser light emitted from the ultraviolet laser light source 3 is detected by the detector 215 and the detected amount of light is represented with the elapse of time (the vertical axis indicates a light intensity I and the horizontal axis indicates time t).

Upon the pattern defect inspection, the stage 2 with the specimen 1 mounted thereon is controlled so as to move by an inspection width of the image sensor 13 within the storage time of the image sensor 13 to thereby obtain a pattern image having tetragonal pixels. Therefore when the amount of light received within the storage time of the image sensor 13 changes, the unevenness of lightness occurs in the detected image.

Figure 8A:
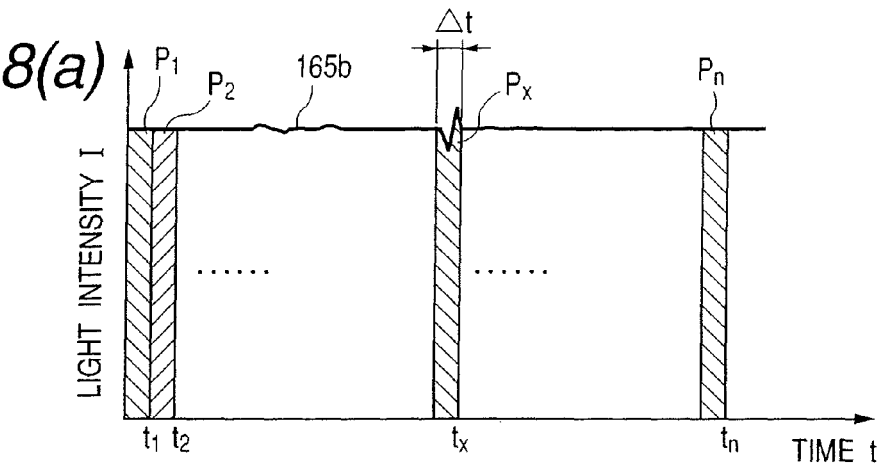
FIGS. 8($a$) and 8($b$) are typical diagrams for describing variations in the output of the ultraviolet laser light source according to the present invention.

FIG. 8(a) is a diagram typically showing the relationship between the time t (t=1~n) at which the stage is moved by an inspection width, and the amount of light p (p=1~n) stored in the image sensor 13. The light-received signal outputted from the detector 215 is integrated by the integration circuit 216 within the storage time of the image sensor 13 and converted into an electric signal, followed by transfer to the comparator 218 for each storage time.

The comparator 218 compares the electric signal sent from the integration circuit 216 with the reference value (Ith) 217 inputted from and set by the input means 18 or the like in advance. When the electric signal sent from the integration circuit 216 is judged to be an abnormal value exceeding an allowable value with respect to the reference value 217, the position of coordinates of the specimen 1 at a time tx thereof is stored in the central processing unit 19. The coordinate position of the specimen 1 can be recognized from a position signal (linear encoder pulse) of the stage 2. Therefore the central processing unit 19 is also capable of inspecting that point again based on the coordinate position data stored in the memory device 20 or the like. Reflecting it on the result of inspection obtained from the comparator 17 or the like allows prevention of disinformation caused by the instabilization of the light source. Further, when the electric signal sent from the integration circuit 216 frequently exceeds the allowable value for the reference value 217, the central processing unit 19 may judge the system lying within the laser light source as faulty and thereby may stop inspecting.

As described above, the central processing unit 19 is capable of detecting the prediction of the life of the ultraviolet laser light source 3 and the malfunction thereof, based on the result of detection of the variation in the amount of laser light detected by the detector (amount-of-light monitor means) 215, and thereby determining whether the inspection should be carried out continuously.

Figure 8B:
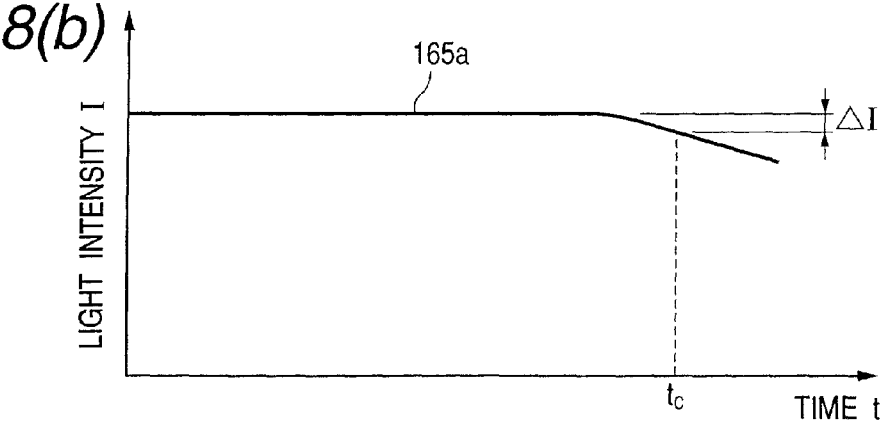

Meanwhile, the excitation laser light L1 is gathered at and applied to the non-linear optical crystal 85 provided within the wavelength converting device 81 of the laser light source 3 to improve the conversion efficiency of the second harmonic wave. Therefore the laser focused-point on the crystal surface is degraded with the elapse of time, and the transmittance of the crystal is reduced. FIG. 8(b) is a typical diagram showing the manner thereof (the relationship between a light intensity I of ultraviolet laser light outputted from the ultraviolet laser light source 3 and the elapse of time t). A reduction in transmittance gradually proceeds during the use of laser and is quickened or made faster with the elapse of time. The output of the ultraviolet laser light emitted from the ultraviolet light source 3 is reduced when the transmittance of the crystal is lowered. Therefore, for example, the central processing unit 19 sends a command to the control device 350 of the ultraviolet laser light source 3 to set the ultraviolet laser light L2 received by the detector 215 to a set value, thereby increasing the source voltage for the excitation laser light L1 so as to adjust the output of the excitation laser light L1. Alternatively, each of the density filters 220 attached to the density adjusting device 210 placed in the illumination optical path is rotated by the motor 200 so as to be set to suitable transmittance. As a result, the transmitted amount of ultraviolet laser light L2 is adjusted. Incidentally, the density adjusting device 210 takes such a construction that it is provided on the stage 250 movable in a Y direction by a motor 251 as shown in FIG. 3 and moved for each predetermined time, thereby making it possible to change a position to apply laser to each of the density filters 220.

However, when the ultraviolet laser light L2 does not reach the set value (when the light intensity I is lowered by ΔI from a constant value 165a) even if the output of the excitation laser light L1 is raised as described above, an unillustrated moving mechanism moves the non-linear optical crystal 85 provided within the wavelength converting device 81 by a predetermined amount to thereby change the position to apply laser light to each density filter. While this work is automatically executed inside the wavelength converting device 81, the central processing unit 19 manages and controls the crystal so that it is not moved freely in the course of the inspection of the specimen 1. About several tens of position coordinates are determined in advance as the positions to apply the laser to the crystal, and the lifetime per one laser-irradiated position is mostly determined according to the internal property of the crystal. When all the laser-irradiated positions are used up, the crystal per se is replaced with another. The number of the laser-irradiated positions for the crystal has been inputted to the central processing unit 19 in advance. When the last laser-irradiated position is reached, the central processing unit 19 produces a warning signal. Incidentally, as another factor responsible for deterioration of the crystal, there is also considered that contaminants floating in the air are attached to the crystal by the irradiation of the laser light to thereby reduce or deteriorate transmittance.

Thus while the central processing unit 19 generates the warning signal when the last position to apply the laser light to the crystal is reached, it may produce a warning signal where the life of the crystal expires when it is used over, for example, 50 hours with the maximum power, e.g., where it is used over 40 hours at which its life is brought to a rate (80%) determined with respect to 50 hours.

Thus in the present invention, a second embodiment according to a defect inspecting apparatus will be explained with reference to FIGS. 9 and 10.

Figure 9:
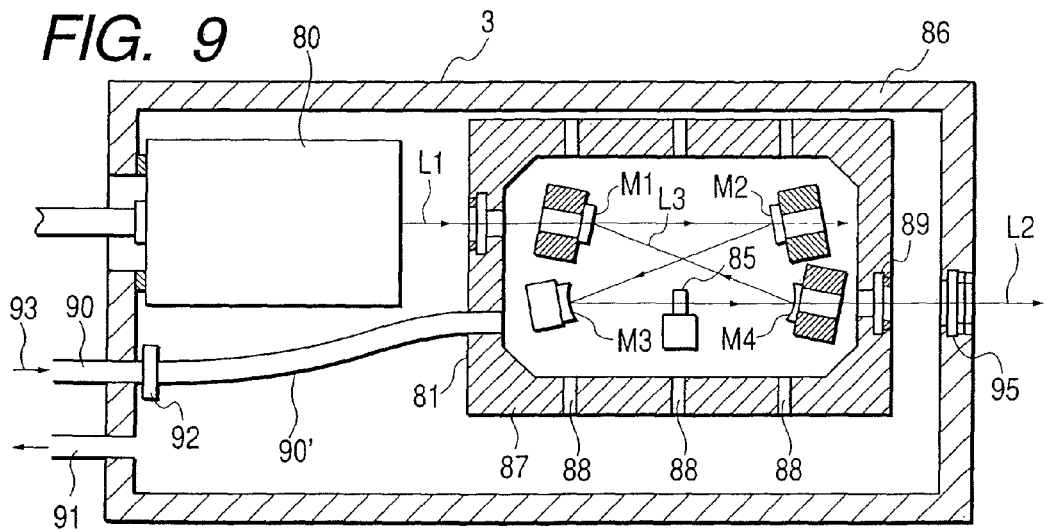
FIG. 9 is a diagram showing a schematic configuration of an ultraviolet laser light source according to the present invention.

FIG. 9 is a diagram showing an ultraviolet laser light source 3 as viewed from a Z direction and shows a schematic structure (section) provided within a container 86. A laser device 80 and a wavelength converting device 81 both constituting an ultraviolet laser light source 3 are first formed as structures provided within the closed container 86. Further, the container 86 is provided with a supply or feed port 90 and an exhaust port 91. A clean gas 93 is supplied to within the container (particularly, a container 87 of the wavelength converting device 81) formed as a closed structure from the feed port 90 through a dustproof filter 92 and a flexible piping 90'. The gas is discharged from the exhaust port 91 through ventilation holes 88 defined in the container 87 and circulated therethrough, thereby cleaning the interior of the container is cleaned inclusive of even the interior of the wavelength converting device 81, whereby the lifetimes of the optical parts and crystal placed inside the container can be made long. In this case, a structure is used wherein connecting cables or the like can detachably be mounted in a state of being independent of the interior thereof. Incidentally, the container 87 of the wavelength converting device 81 is formed as a closed structure without providing the ventilation holes 88. Further, the piping 90' is omitted and the clean gas 93 is supplied to within only the container 86 from the feed port 90 through the dustproof filter 92 and discharged from the exhaust port 91 to circulate it. By doing so, the interior of the container 86 is cleaned and hence the optical parts placed inside the container 86 can be made long-lived. Particularly, the clean gas 93 is circulated between a transparent window 89 through which the ultraviolet laser light L2 is outputted from the wavelength converting device 81 and a transparent window 95 defined in the container 86, through which the ultraviolet laser light is outputted from the ultraviolet laser light source 3, whereby the lifetime of each optical part lying between the transparent windows 89 and 95 inclusive of the transparent windows 89 and 95 can be made long.

Figure 10:
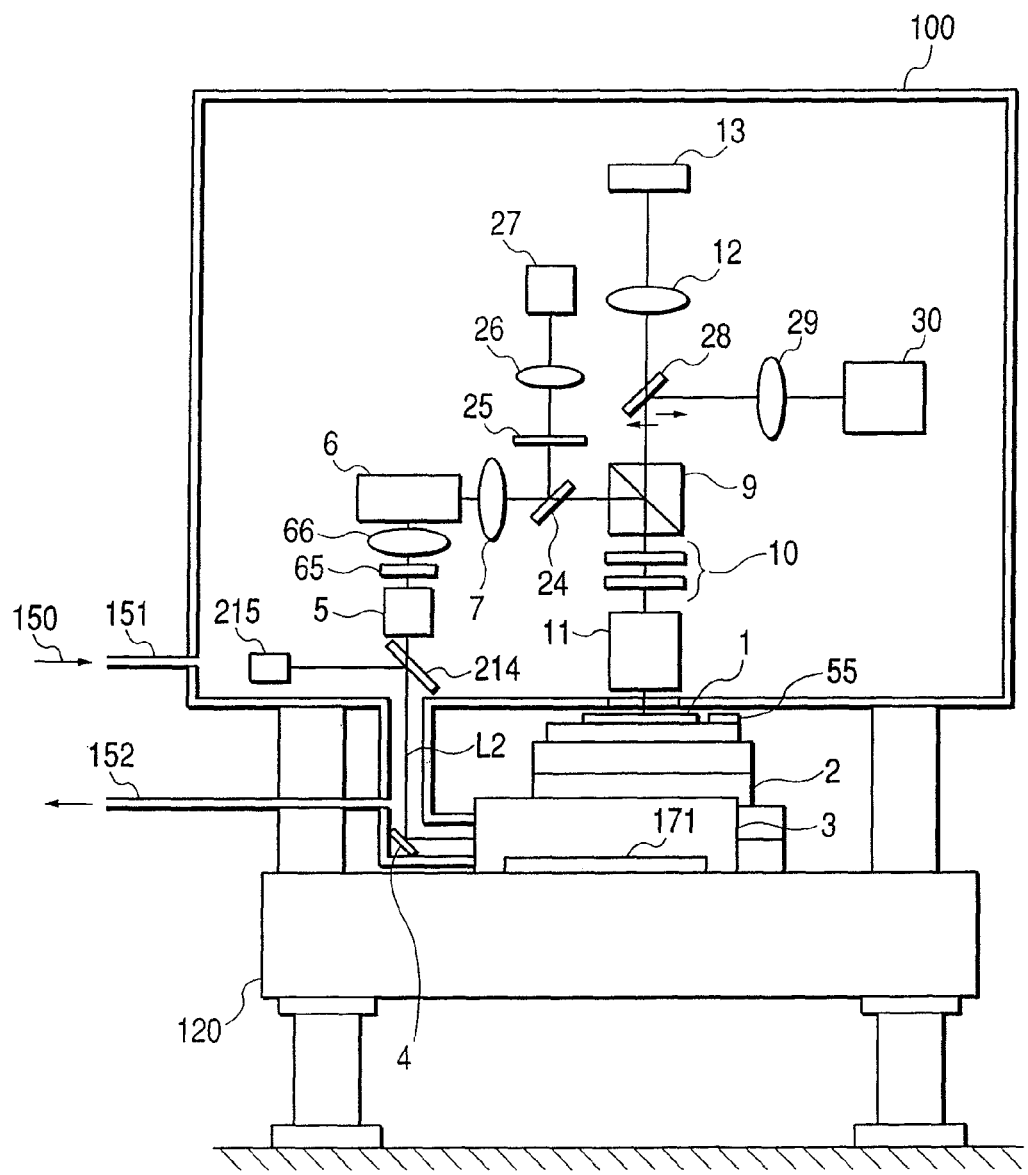
FIG. 10 is a configurational diagram illustrating a second embodiment of a pattern defect inspecting apparatus according to the present invention.

In addition to the above, the whole optical system including an illumination optical system 5 through 11, a detection optical system 9 through 13, etc. is covered with a cover (container) 100 as shown in FIG. 10. A clean gas 150 is supplied to within the optical system from a feed port 151 and set to such a flow rate as not to exert an influence such as fluctuations on each internal optical system, followed by discharge from an exhaust port 152 to circulate it. Thus each optical part or the like provided inside the optical system can also be made long-lived as well as an ultraviolet laser light source 3.

Incidentally, since the clearance defined between a specimen 1 and an objective lens 11 cannot be increased, an air curtain is provided therebetween to bring it to negative pressure. Thus the interior of the cover (container) 100 can be held in an atmosphere of the clean gas.

The ultraviolet laser light source 3, stage 2, and illumination optical system 4 through 11 and detection optical system 9 through 13 covered with the cover (container) 100 are mounted on an antivibration table 120. In particular, the ultraviolet laser light source 3 is positioned by being engaged or fit in an engaging or fitting member 171 provided on the antivibration table 120, thus making it possible to place it on the antivibration table 120. As a result, when the ultraviolet laser light source 3 reaches the end of its life and is thereby replaced with another, a new ultraviolet laser light source 3 can be placed on the antivibration table 120 so that the light-outgoing optical axis of the ultraviolet laser light source substantially coincides with the optical axis of the illumination optical system.

In the present invention in this manner, in order to facilitate an optical-axis adjustment, the outside of the container for the ultraviolet laser light source 3 is first mechanically positioned by use of the engaging or fitting member 171 or the like. Next, for example, 4-division type light-detecting devices are used for a detector 215, and the mirror 4 or the like is precisely moved by an unillustrated actuator or the like so that the outputs of the light-detecting devices lying in X and Z directions become equal to each other, whereby the adjustment to the optical axis can be simplified.

Further, when all the positions to apply the laser to the non-linear optical crystal 85 are used up within the wavelength converting device 81, the entire ultraviolet laser light source 3, the whole wavelength converting device 81, or the non-linear optical crystal 85 lying within the wavelength converting device 81 is replaced with another. Thus the whole ultraviolet laser light source 3 or the whole wavelength converting device 81 may be replaced with another because the time required to replace it with another can be shortened. In either case, the position to apply the ultraviolet laser light L2 with respect to the container 86 or the illumination optical system changes after the replacement of the crystal or the like. It is therefore necessary to re-align the optical axis of the ultraviolet laser light source 3 with that of the illumination optical system (inspecting apparatus).

Figure 11A:
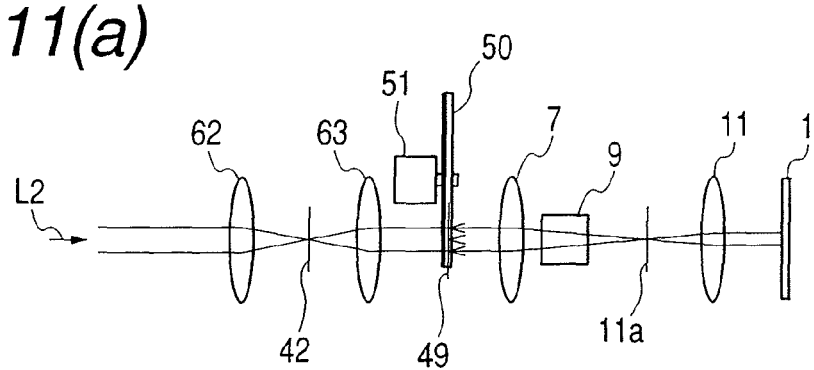
FIGS. 11($a$) to 11($c$) are typical diagrams depicting another embodiment of a coherence reduction optical system according to the present invention.

Another embodiment of the coherence reduction optical system 6 will next be described. In the present embodiment, as shown in FIG. 11(a), a circular diffusion plate (rotating optical device) 50 is placed in a focal position 49 in an optical path in place of the scan mirrors (swinging optical devices) 41 and 44 shown in FIG. 4 and rotated at high speed by means of a motor 51. Namely, the diffusion plate 50 whose surface has been processed to suitable roughness, is placed in the focal position 49 of a lens 63 (and a lens 7). An ultraviolet laser spot which converges on a pupil 11a of an objective lens 11 with a certain degree of expansion, is scanned under the rotation of the motor 51 to reduce spatial coherence, thereby reducing coherence.

Figure 11B:
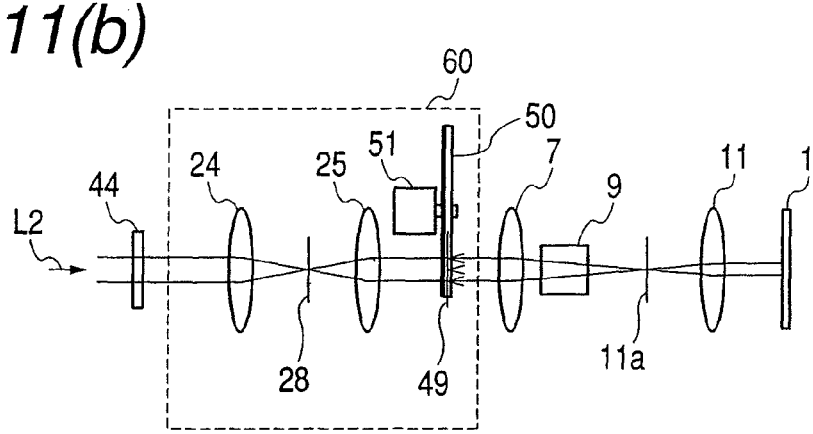

In FIG. 11(b) as well, a relay system 60 including a diffusion plate (rotating optical device) 50 is newly provided between a scan mirror 44 and a lens 7. The diffusion plate (rotating optical device) 50 is rotated in combination with the scan mirrors (swinging optical devices) 41 and 44 at high speed by means of a motor 51 to thereby achieve a reduction in coherence.

Figure 11C:
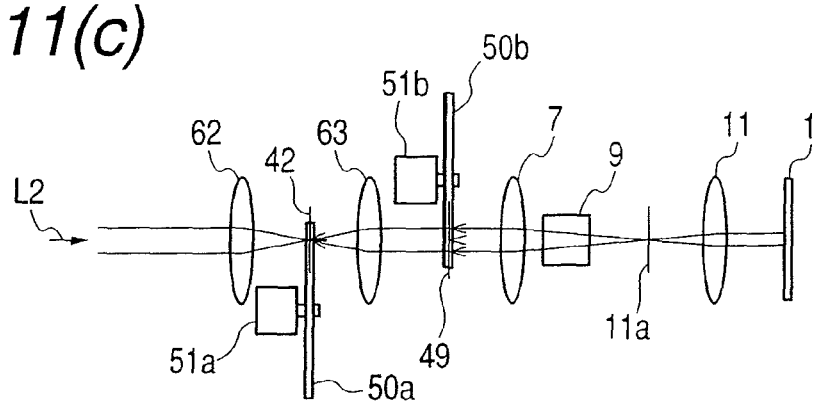

Further, FIG. 11(c) shows a case in which two types of diffusion plates 50a and 50b, and motors 51a and 51b for respectively rotating them are used. One diffusion plate 50a is placed in a focal position 42 of a lens 62 (and a lens 63), i.e., a position conjugated with respect to a pupil 11a of an objective lens, whereas the other diffusion plate 50b is placed in a focal position 49 of a lens 7 (and the lens 63) in a manner similar to FIGS. 11(a) and 11(b). They are rotated (in the same direction or opposite direction) at high speed by means of the motors 51a and 51b to thereby reduce coherence. While ultraviolet laser light is expanded to some extent by the diffusion plate 50, the lens 7 will be selected as a lens having a numerical aperture, which covers it. The detailed specifications of the diffusion plate 50 will be determined according to experiments. Incidentally, it is needless to say that the rotating cycles of the scan mirrors 41 and 44 and the diffusion plate 50 are set in accordance with the storage time of the image sensor 13.

Figure 12:
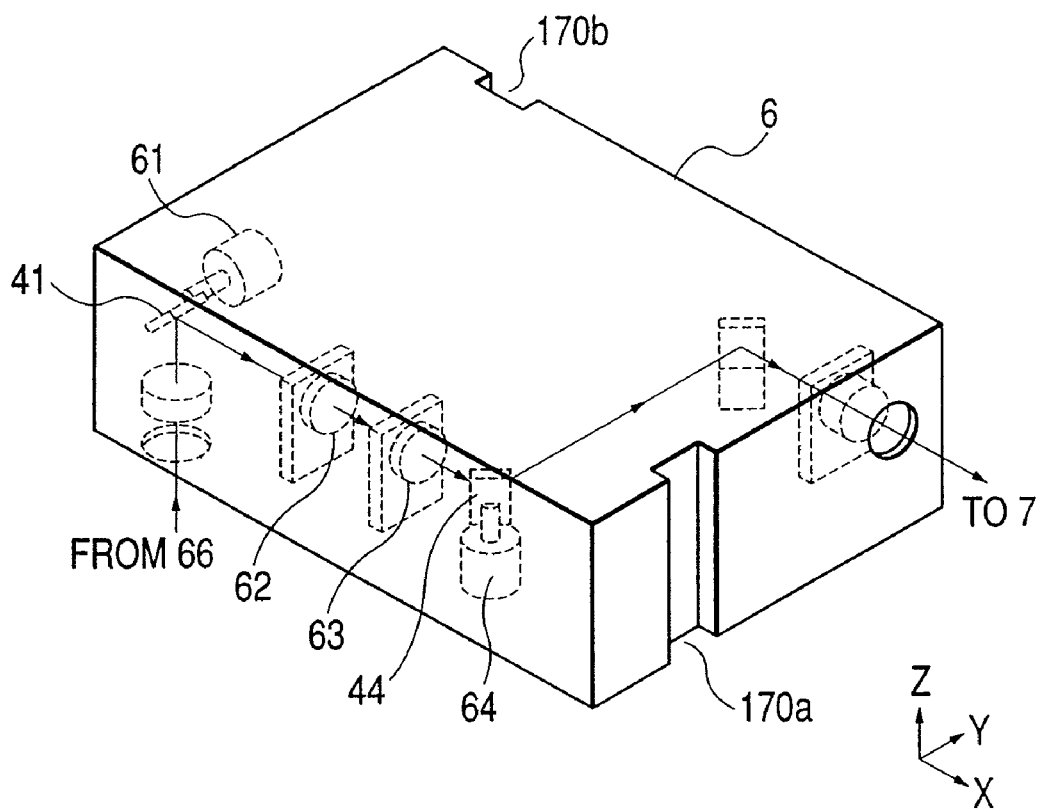
FIG. 12 is a perspective view showing a further embodiment of a unitized coherence reduction optical system according to the present invention.

The coherence reduction optical system is not limited to the above-described construction. A polyhedral mirror or the like may be used in place of the scan mirrors. Using a two-dimensional scan mirror such as a DMD (Digital Mirror Device) or the like enables the lightening of a mechanism portion. These coherence reduction optical systems 6 can also be attached in unitized form as shown in FIG. 12. In this case, there is an effect in that an exchange working time can be shortened owing to the provision of positioning means 170a and 170b comprising engaging portions or fitting portions for facilitating the positioning of units to an illumination optical system (inspecting apparatus) at their corresponding ends.

According to the present invention as described above, an advantageous effect is brought about in that micro patterns can be implemented with high resolution and a stable pattern defect inspection can be achieved with high reliability, with ultraviolet laser light as a light source.

According to the present invention as well, even if an output variation is produced from the ultraviolet laser light source due to some influence during inspection, inspection information at that time can be stored and reflected on the result of inspection. Thus the occurrence of disinformation caused by the influence of an output variation in laser can easily be analyzed, and re-inspection can also be carried out, thus making it possible to prevent the inspection from being missed and improve the reliability of the inspection.

Further, according to the present invention, an advantageous effect is brought about in that the work of replacing each optical part or the like with another can also be carried out with ease, and a clean gas is circulated through the interior of an optical system to enable the prevention of contaminants peculiar to ultraviolet rays from being attached to the optical parts, whereby a pattern defect inspecting apparatus can be made long-lived.

While the present invention has been described with reference to the illustrative embodiments, this description is not intended to be construed in a limiting sense. Various modifications of the illustrative embodiments, as well as other embodiments of the invention, will be apparent to those skilled in the art on reference to this description. It is therefore contemplated that the appended claims will cover any such modifications or embodiments as fall within the true scope of the invention.

What is claimed is:

1. An apparatus for inspecting defects, comprising:
   a table which mounts a specimen to be inspected and movable in a plane;
   an ultraviolet light source which includes a solid-state laser device and a wavelength converter device and emits an ultraviolet laser beam;
   an illuminating unit which illuminates the specimen mounted on the table with light emitted from the ultraviolet light source and provided with a first polarization condition;
   a detecting unit which detects light reflected from the specimen illuminated by the illuminating unit, said light reflected from the specimen is a second polarization condition; and
   a processing unit which processes signals output from the detecting unit by the detection of the reflected light and outputs information about defects detected on the specimen;
   wherein the solid-state laser device and the wavelength converter device of the ultraviolet light source are disposed in a first closed container supplied with clean gas and separated from the table which mounts the specimen and the detecting unit which are disposed outside the first container, and
   wherein the wavelength converter is disposed in a second closed container which is in the first closed container.

2. An apparatus according to claim 1, further comprising a polarization condition controller which provides the first polarization condition and the second polarization condition.

3. An apparatus according to claim 2, wherein the polarization condition controller includes a ½ wavelength plate and a ¼ wavelength plate.

4. An apparatus according to claim 1, wherein the ultraviolet light source emits the ultraviolet laser beam having a wavelength of 266 nm.

5. An apparatus according to claim 1, wherein the detecting unit detects an optical image of the specimen and the processing unit processes the image detected by the detecting unit.

6. A method for inspecting defects, comprising the steps of:
   emitting an ultraviolet laser beam from an ultraviolet light source which includes a solid-state laser device and a wavelength converter device;
   illuminating a specimen with the ultraviolet light in which a polarization condition of the ultraviolet light is controlled;
   controlling a polarization condition of light reflected from the specimen illuminated by the polarization condition controlled ultraviolet light;
   detecting the light reflected from the specimen by a detecting unit;
   processing signals which are output from the detecting unit; and
   outputting information about the defects detected on the specimen;
   wherein the solid-state laser device and the wavelength converter device of the ultraviolet light source are disposed in a first closed supplied with clean gas and separated from the specimen and the detection unit which are disposed outside the first container, and
   wherein the wavelength converter is disposed in a second closed container which is in the first closed container.

7. A method according to claim 6, wherein the ultraviolet laser beam which illuminates the specimen has a wavelength of 266 nm.

8. A method according to claim 6, wherein in the step of detecting the light, an optical image of the specimen is detected, and in the step of processing the detected light, the detected optical image is processed.

* * * * *